US00PP30562P2

(12) United States Plant Patent
Danziger

(10) Patent No.: US PP30,562 P2
(45) Date of Patent: Jun. 4, 2019

(54) ***GAURA* PLANT NAMED 'DGAUR137'**

(50) Latin Name: *Gaura lindheimeri*
Varietal Denomination: DGAUR137

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm, Beit Dagan (IL)

( * ) Notice: Subject to any disclaimer, the term of this patent is extended or adjusted under 35 U.S.C. 154(b) by 0 days.

(21) Appl. No.: 15/932,284

(22) Filed: Feb. 16, 2018

(51) Int. Cl.
*A01H 5/02* (2018.01)

(52) U.S. Cl.
USPC ..... Plt./432

(58) Field of Classification Search
USPC ..... Plt./432
See application file for complete search history.

*Primary Examiner* — Annette H Para
(74) *Attorney, Agent, or Firm* — C. A. Whealy

(57) ABSTRACT

A new and distinct cultivar of *Gaura* plant named 'DGAUR137', characterized by its compact, upright to outwardly spreading plant habit; moderately vigorous growth habit; freely basal branching habit; dark green-colored leaves; early and freely flowering habit; light red purple-colored flowers; and good garden performance.

2 Drawing Sheets

Botanical designation: *Gaura lindheimeri.*
Cultivar denomination: 'DGAUR137'.

BACKGROUND OF THE INVENTION

The present invention relates to a new and distinct cultivar of *Gaura* plant, botanically known as *Gaura lindheimeri* and hereinafter referred to by the name 'DGAUR137'.

The new *Gaura* is a product of a planned breeding program conducted by the Inventor in Moshav Mishmar Hashiva, Israel. The objective of the breeding program is to create new semi-upright *Gaura* plants with attractive leaf and flower coloration.

The new *Gaura* plant originated from an open-pollination in October, 2010 in Moshav Mishmar Hashiva, Israel of a proprietary selection of *Gaura lindheimeri* identified as code designation GO-Z-23, not patented, as the female, or seed, parent with an unknown selection of *Gaura lindheimeri* as the male, or pollen, parent. The new *Gaura* plant was discovered and selected by the Inventor as a single flowering plant from within the progeny of the stated open-pollination in a controlled environment in Moshav Mishmar Hashiva, Israel during the summer of 2011.

Asexual reproduction of the new *Gaura* plant by vegetative cuttings in a controlled environment in Moshav Mishmar Hashiva, Israel since September, 2011 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DGAUR137'. These characteristics in combination distinguish 'DGAUR137' as a new and distinct *Gaura* plant:

1. Compact, upright to outwardly spreading plant habit.
2. Moderately vigorous growth habit.
3. Freely basal branching habit.
4. Dark green-colored leaves.
5. Early and freely flowering habit.
6. Light red purple-colored flowers.
7. Good garden performance.

Plants of the new *Gaura* can be compared to plants of the female parent selection. Plants of the new *Gaura* differ from plants of the female parent selection in the following characteristics:

1. Plants of the new *Gaura* are more compact than plants of the female parent selection.
2. Plants of the new *Gaura* are more freely branching and denser than plants of the female parent selection.
3. Plants of the new *Gaura* have shorter lateral branches than plants of the female parent selection.
4. Plants of the new *Gaura* flower earlier than plants of the female parent selection.

Plants of the new *Gaura* can be compared to plants of *Gaura lindheimeri* 'KLEGL06261', not patented. In side-by-side comparisons, plants of the new *Gaura* differ from plants of 'KLEGL06261' in the following characteristics:

1. Plants of the new *Gaura* have broader leaves than plants of 'KLEGL06261'.
2. Plants of the new *Gaura* have slightly larger flowers than plants of 'KLEGL06261'.
3. Flowers of plants of the new *Gaura* are brighter red purple in color than flowers of plants of 'KLEGL06261'.

Plants of the new *Gaura* can be compared to plants of *Gaura lindheimeri* 'KLEAU04263', not patented. In side-by-side comparisons, plants of the new *Gaura* differ from plants of 'KLEAU04263' in the following characteristics:

1. Plants of the new *Gaura* have broader leaves than plants of 'KLEAU04263'.

2. Plants of the new *Gaura* flower earlier than plants of 'KLEAU04263'.
3. Flowers of plants of the new *Gaura* are brighter red purple in color than flowers of plants of 'KLEAU04263'.

BRIEF DESCRIPTION OF THE PHOTOGRAPHS

The accompanying colored photographs illustrate the overall appearance of the new *Gaura* plant showing the colors as true as it is reasonably possible to obtain in colored reproductions of this type. Colors in the photographs may differ slightly from the color values cited in the detailed botanical description which accurately describe the colors of the new *Gaura* plant.

The photograph on the first sheet is a side perspective view of a typical plant of 'DGAUR137' grown in a container.

The photograph on the second sheet is a close-up view of typical flowers of 'DGAUR137'.

DETAILED BOTANICAL DESCRIPTION

The aforementioned photographs and following observations, measurements and values describe plants grown during the late spring and early summer in 13-cm containers in an outdoor nursery in Moshav Mishmar Hashiva, Israel and under cultural practices typical of commercial *Gaura* production. During the production of the plants, day temperatures ranged from 18° C. to 26° C. and night temperatures ranged from 12° C. to 17° C. Plants were seven weeks old when the photographs and description were taken. In the following description, color references are made to The Royal Horticultural Society Colour Chart, 2007 Edition, except where general terms of ordinary dictionary significance are used.

Botanical classification: *Gaura lindheimeri* 'DGAUR137'.

Parentage:

*Female, or seed, parent*.—Proprietary selection of *Gaura lindheimeri* identified as code designation GO-Z-23, not patented.

*Male or pollen parent*.—Unknown selection of *Gaura lindheimeri*, not patented.

Propagation:

*Type*.—By vegetative cuttings.

*Time to initiate roots, summer*.—About 14 to 16 days at temperatures about 27.5° C.

*Time to produce a rooted young plant, summer*.—About 17 days at temperatures about 27.5° C.

*Root description*.—Medium in thickness, fleshy; typically white in color, actual color of the roots is dependent on substrate composition, water quality, fertilizer type and formulation, substrate temperature and physiological age of roots.

*Rooting habit*.—Freely branching; medium density to dense.

Plant description:

*Plant and growth habit*.—Herbaceous perennial; compact, upright and outwardly spreading plant habit; broad inverted triangle; freely basal branching habit with about six to eight primary lateral branches developing per plant, pinching enhances lateral branch development; dense and bushy plant form; moderately vigorous growth habit.

*Plant height*.—About 25 cm to 35 cm.

*Plant diameter*.—About 23 cm.

Lateral branch description:

*Length*.—About 35 cm.

*Diameter*.—About 2 mm.

*Internode length*.—About 2 cm to 3 cm.

*Strength*.—Strong; flexible.

*Aspect*.—Upright to outwardly spreading.

*Texture*.—Smooth, glabrous.

*Color, developing*.—Close to 137B.

*Color, developed*.—Close to 137C.

Leaf description:

*Arrangement*.—Alternate, simple; sessile.

*Length*.—About 6 cm to 8 cm.

*Width*.—About 7 mm to 10 mm.

*Shape*.—Elongated oval.

*Apex*.—Narrowly acute.

*Base*.—Attenuate.

*Margin*.—Entire.

*Texture, upper and lower surfaces*.—Smooth, glabrous.

*Venation pattern*.—Pinnate.

*Color*.—Developing and fully expanded leaves, upper surface: Close to N137A; venation, close to 138B tinged with close to between 59C and 60B. Developing and fully expanded leaves, lower surface: Close to N137B; venation, close to 138B.

Flower description:

*Flower arrangement and habit*.—Single flowers arranged on terminal and axillary racemes; freely flowering habit with about seven to nine open flowers per inflorescence; flowers face mostly outwardly.

*Fragrance*.—None detected.

*Natural flowering season*.—Plants flower continuously during the spring and summer in Israel.

*Flower longevity*.—Individual flowers last about three to four days on the plant; flowers not persistent.

*Inflorescence height*.—About 7 cm to 9 cm.

*Inflorescence diameter*.—About 4 cm.

*Flower diameter*.—About 3 cm.

*Flower depth (height)*.—About 1.8 cm.

*Flower buds*.—Length: About 1.2 cm to 1.5 cm. Diameter: About 2 mm. Shape: Oblong. Color: Close to 59A.

*Petals*.—Arrangement: Four in a single whorl. Lobe length: About 1.5 cm. Lobe width: About 9 mm. Tube length: About 1.5 cm. Tube diameter: About 2 mm. Shape: Elliptical. Apex: Broadly acute. Base: Attenuate. Margin: Entire. Texture, upper and lower surfaces: Smooth, glabrous. Color: When opening, upper and lower surfaces: Close to 63A. Fully opened, upper surface: Close to 63B; color becoming closer to 75C with development. Fully opened, lower surface: Close to 63B; color becoming closer to 68B with development.

*Sepals*.—Arrangement: Four in a single whorl. Length: About 1.5 cm. Width: About 2 mm. Shape: Ligulate; undulating and reflexed. Apex: Acute. Base: Truncate. Margin: Entire. Texture, upper and lower surfaces: Smooth, glabrous. Color, upper surface: Distally, close to 59A; proximally, close to 60B. Color, lower surface: Distally, close to 59A; proximally, close to N34A.

*Pedicels*.—Length: About 13.5 cm. Diameter: About 3 mm. Strength: Moderately strong. Aspect: Mostly upright. Texture: Smooth, glabrous. Color: Close to 137B.

*Reproductive organs*.—Stamens: Quantity: Eight per flower. Filament length: About 1.2 cm. Filament color: Distally, close to 64B; proximally, close to 62C. Anther shape: Ovate. Anther length: About 3 mm. Anther color: Close to N77A. Pollen amount: Moderate. Pollen color: Close to 2B. Pistils: Quantity: One per flower. Pistil length: About 1.4 cm to 1.6 cm. Style length: About 1.3 cm to 1.5 cm. Style color: Close to 64B; becoming closer to 62C with development. Stigma shape: Four-lobed. Stigma color: Close to 150D. Ovary length: About 1 cm. Ovary diameter: About 1 mm. Ovary shape: Ligulate. Ovary color: Close to 59A. Seeds and fruits: Seed and fruit development have not been observed on plants of the new *Gaura* to date.

Garden performance: Plants of the new *Gaura* have been observed to have good garden performance and tolerate wind, rain and temperatures ranging from about −10° C. to about 40° C.

Pathogen & pest resistance: To date, plants of the new *Gaura* have not been observed to be resistant to pathogens and pests common to *Gaura* plants.

It is claimed:

1. A new and distinct *Gaura* plant named 'DGAUR137' as illustrated and described.

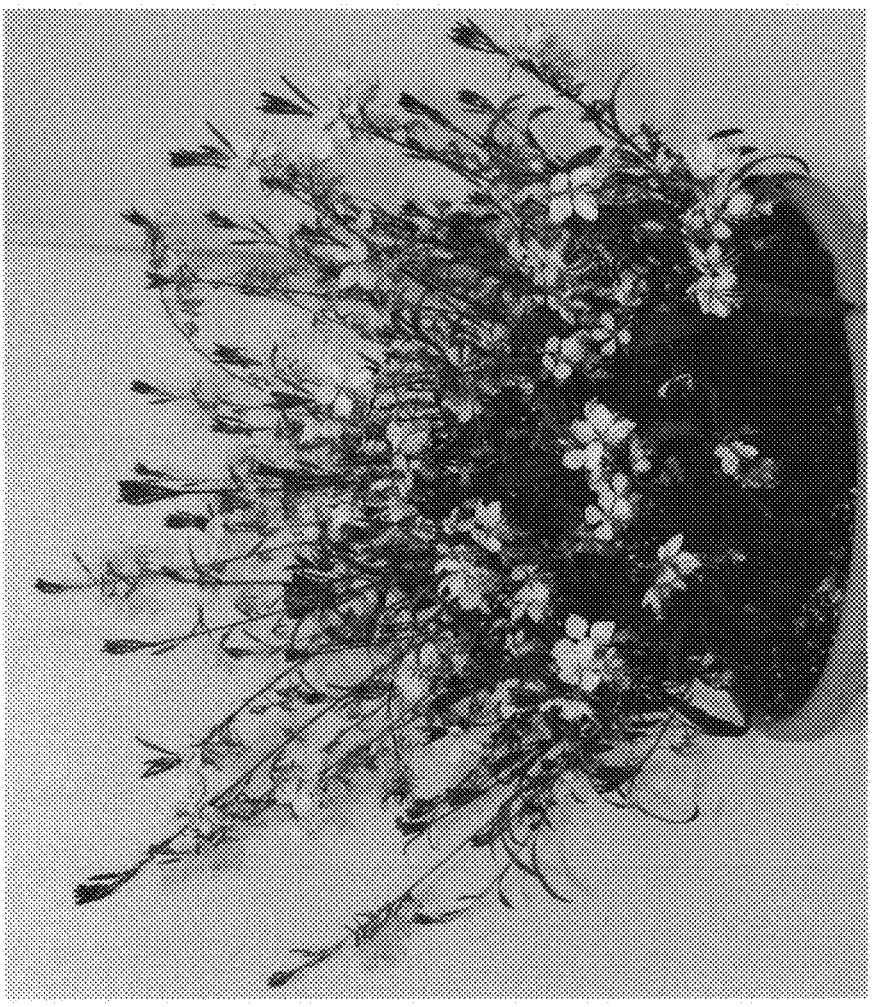

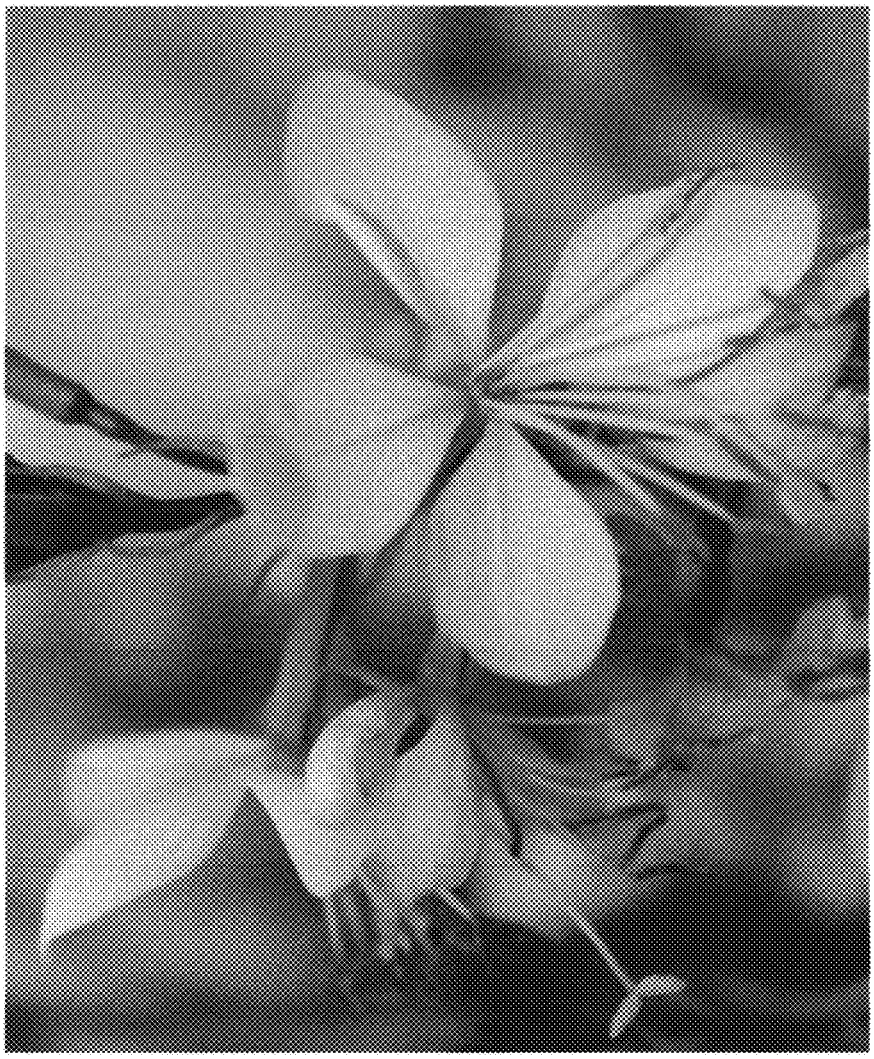

* * * * *